(12) United States Patent
Inoue et al.

(10) Patent No.: US 8,581,973 B2
(45) Date of Patent: Nov. 12, 2013

(54) ENDOSCOPIC DIAGNOSIS SUPPORT METHOD, ENDOSCOPIC DIAGNOSIS SUPPORT APPARATUS AND ENDOSCOPIC DIAGNOSIS SUPPORT PROGRAM

(75) Inventors: Ryoko Inoue, Tokyo (JP); Tetsuo Nonami, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1874 days.

(21) Appl. No.: 11/639,687

(22) Filed: Dec. 15, 2006

(65) Prior Publication Data
US 2007/0135715 A1 Jun. 14, 2007

Related U.S. Application Data

(63) Continuation of application No. PCT/JP2006/308330, filed on Apr. 20, 2006.

(30) Foreign Application Priority Data

Jun. 1, 2005 (JP) ................................. 2005-162023

(51) Int. Cl.
H04N 7/18 (2006.01)
A62D 1/04 (2006.01)

(52) U.S. Cl.
USPC ............................................. 348/77; 348/65

(58) Field of Classification Search
USPC ..................................................... 348/65, 77
See application file for complete search history.

(56) References Cited

U.S. PATENT DOCUMENTS

2002/0177779 A1* 11/2002 Adler et al. ................... 600/476
2004/0010375 A1* 1/2004 Schomacker et al. .......... 702/19
2004/0071352 A1* 4/2004 Mizoguchi et al. ........... 382/233
2004/0225223 A1* 11/2004 Honda et al. .................. 600/476
2007/0165932 A1* 7/2007 Nishimura et al. ........... 382/128

FOREIGN PATENT DOCUMENTS

CN 1509152 A 6/2004
EP 1 416 262 A2 5/2004
(Continued)

OTHER PUBLICATIONS

European Official Action dated Dec. 27, 2011 from corresponding European patent application 06745511.3.
(Continued)

Primary Examiner — Kevin Bates
Assistant Examiner — Tom Y Chang
(74) Attorney, Agent, or Firm — Scully, Scott, Murphy & Presser, P.C.

(57) ABSTRACT

Provided are an endoscopic diagnosis support method, an endoscopic diagnosis support apparatus, and an endoscopic diagnosis support program, all of which are capable of extracting an image picking up a bleeding region easily and accurately from among a large number of endoscopic images picked up by an endoscope observation apparatus by calculating a tone from a color signal of each of plural image zones obtained by dividing the endoscopic image; and discerning an image zone including a bleeding region by judging a difference among each of the plural image zones based on a tone of the calculated each image zone in the endoscopic diagnosis support apparatus for supporting an endoscopic diagnosis performed based on an endoscopic image picked up by an endoscope observation apparatus.

18 Claims, 11 Drawing Sheets

(56) References Cited

FOREIGN PATENT DOCUMENTS

| | | |
|---|---|---|
| JP | 59-032824 | 2/1984 |
| JP | 1-101962 | 4/1989 |
| JP | 2-124131 | 5/1990 |
| JP | 2001-37718 | 2/2001 |
| JP | 2005-192880 | 7/2005 |
| JP | 2002-165757 | 6/2006 |
| WO | WO 02/073507 A2 | 9/2002 |
| WO | WO 2004/051288 A1 | 6/2004 |

OTHER PUBLICATIONS

Japanese Office Action dated Mar. 22, 2011 of corresponding JP Application No. 2005-162023 together with an English translation.

* cited by examiner

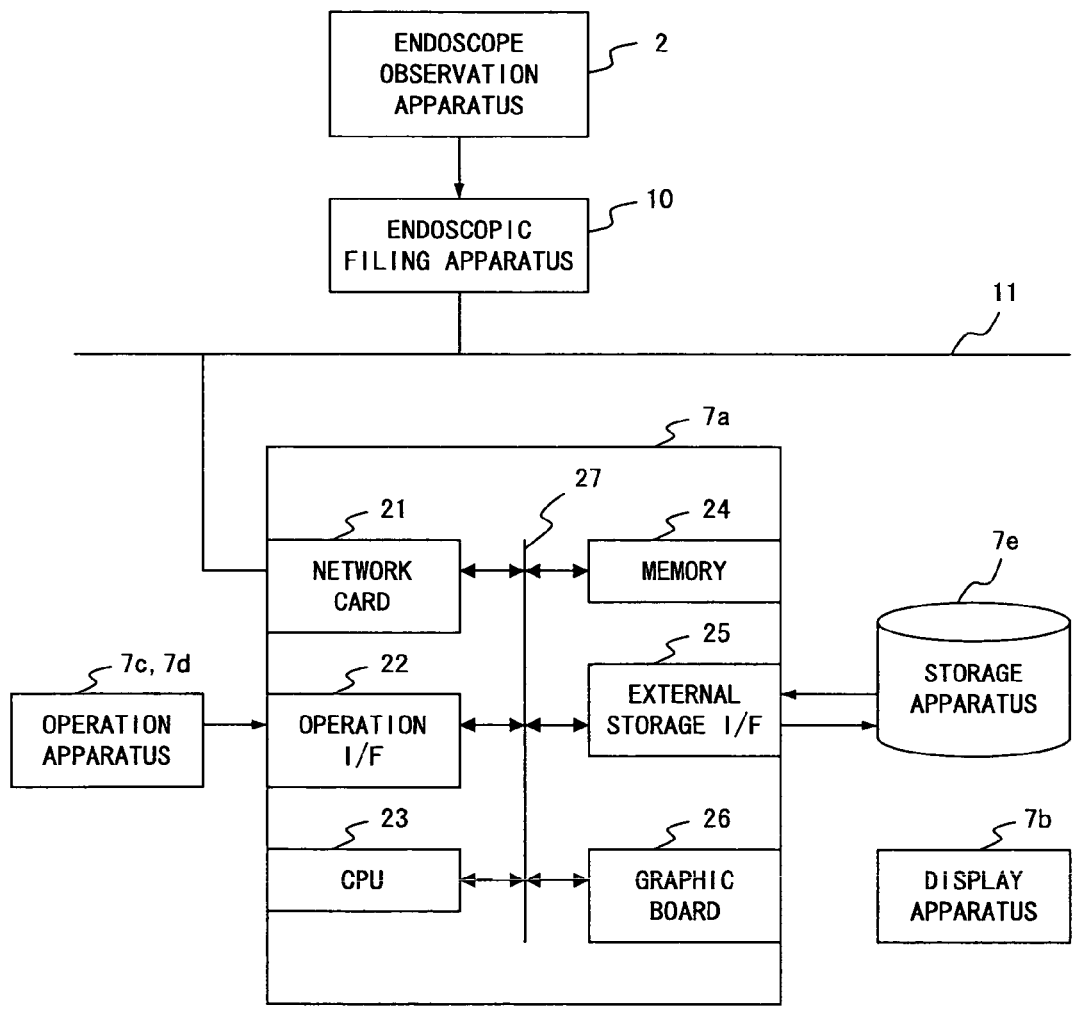
F I G. 2

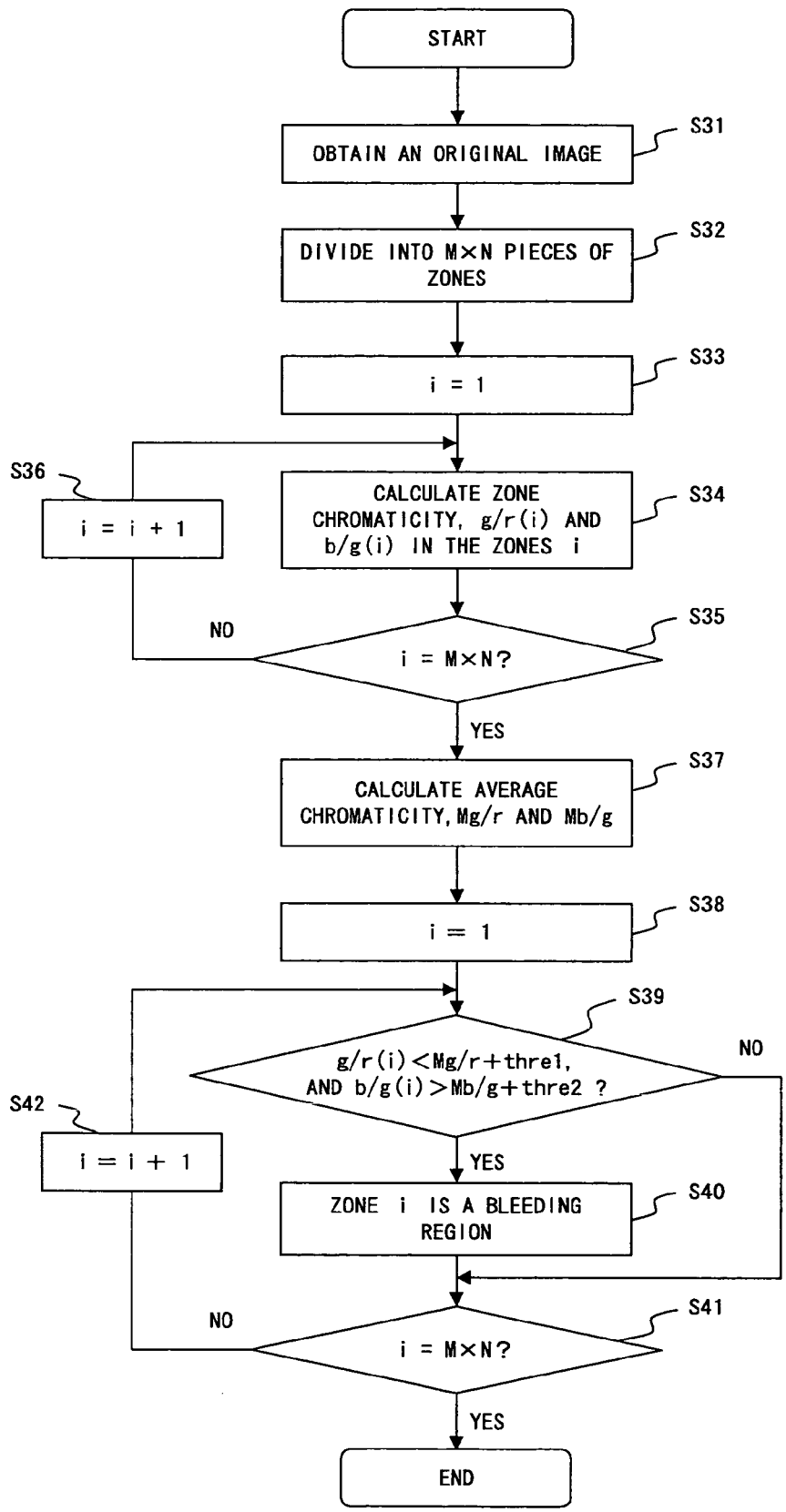
F I G. 3

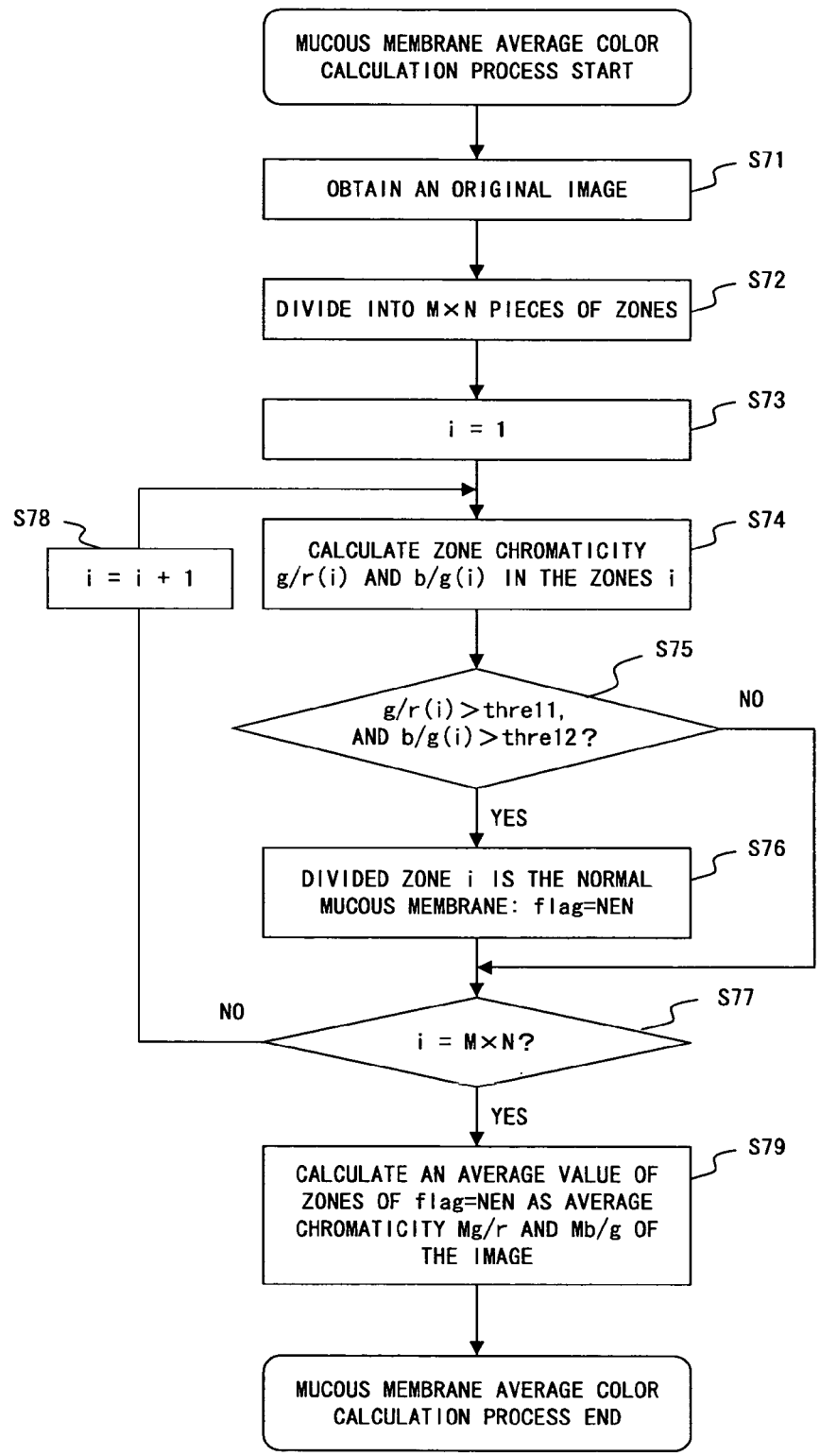
F I G. 7

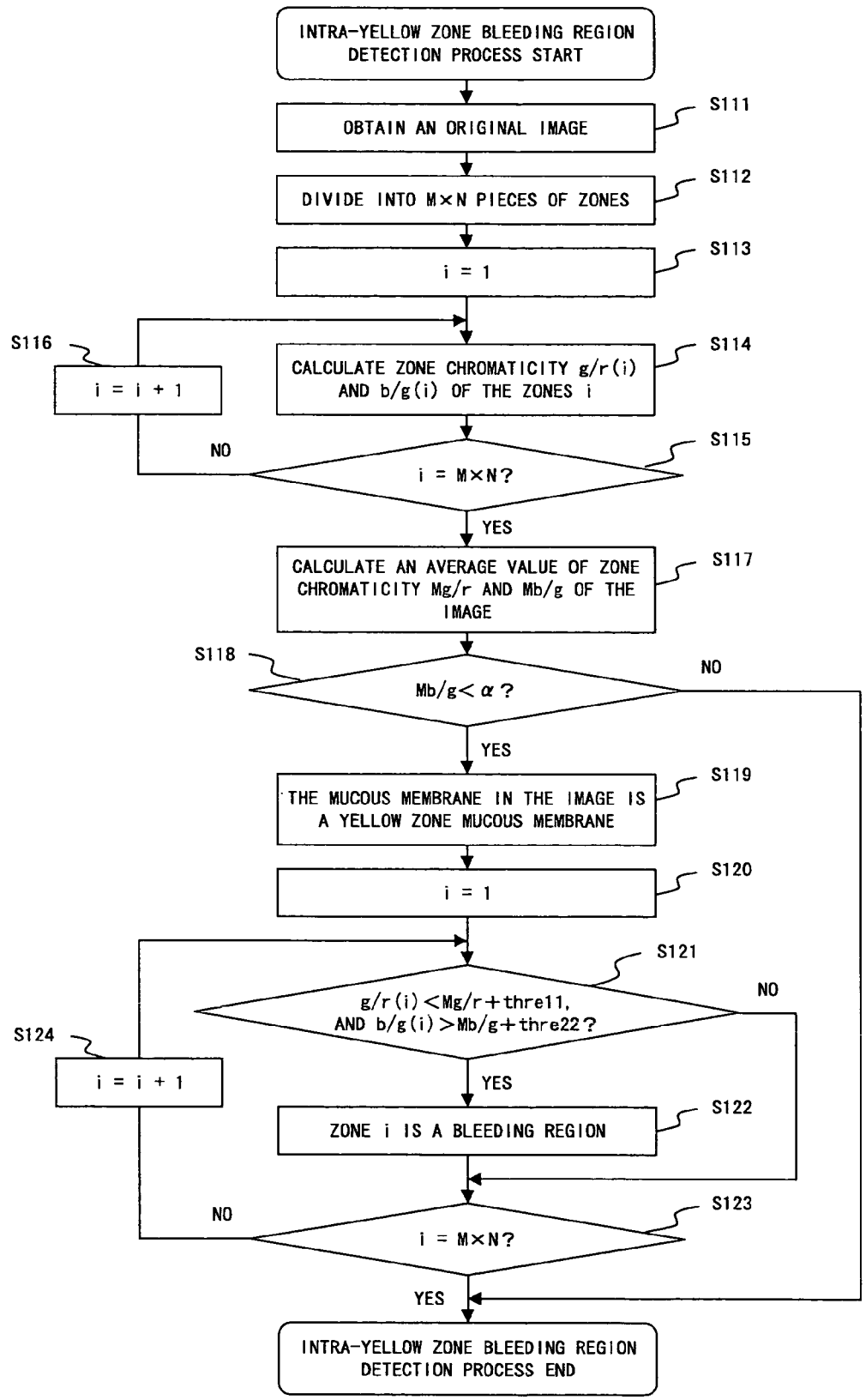
F I G. 1 1

ENDOSCOPIC DIAGNOSIS SUPPORT METHOD, ENDOSCOPIC DIAGNOSIS SUPPORT APPARATUS AND ENDOSCOPIC DIAGNOSIS SUPPORT PROGRAM

CROSS REFERENCE TO RELATED APPLICATIONS

This is a Continuation Application of PCT Application No. PCT/JP2006/308330, filed on Apr. 20, 2006, which was not published under PCT Article 21(2) in English.

This application is based upon and claims the benefit of priority from the prior Japanese Patent Application No. 2005-162023, filed Jun. 1, 2005, the contents of which are incorporated by this reference.

BACKGROUND OF THE INVENTION

1. Field of the Invention

The present invention relates to an endoscopic diagnosis support method, an endoscopic diagnosis support apparatus, and an endoscopic diagnosis support program, all of which are for supporting an endoscopic diagnosis carried out based on an endoscopic image picked up by an endoscopic observation apparatus for picking up images of an observation region by autonomously moving within a lumen, and in particular to the endoscopic diagnosis support method, endoscopic diagnosis support apparatus and endoscopic diagnosis support program for supporting an endoscopic diagnosis by identifying a bleeding region based on an endoscopic image.

2. Description of the Related Art

Endoscopes have conventionally been widely used in medical practice and industrial fields. Among the recent medical practice-use endoscopes exists a so called capsule endoscope which no longer requires an insertion part by forming the scope as a capsule configuration. The capsule endoscope is configured to comprise an image pickup function and a radio communication function, and is swallowed by a patient to be observed (i.e., examined), followed by picking up images of respective organs such as stomach and intestine in an orderly fashion and likewise transmitting the pickup image information (i.e., electronic data representing an image) externally through radio waves during an observation period until it is naturally ejected from the human body.

Thusly wirelessly transmitted image information is received by a receiver equipped externally to the body of the patient and stored in predetermined memory, followed by a physician utilizing for diagnosis, et cetera, by reading the information and displaying in such as a display apparatus on an as required basis according to the configuration.

Such a capsule endoscope, however, has an observation period extending eight hours or more than ten hours since the observation period spans from a patient swallowing it to a natural ejection thereof, resulting in the number of pieces of image information obtained by picking up images during such a long hours becoming enormous.

Due to this, a grasp of such an enormous number of pieces of image information in a short time available in a stage such as diagnosis is never easy, nor is it easy to find a desired piece of image information, such as image information related to an image photographing an disorder region, et cetera, from the enormous number thereof.

Meanwhile, not just pertaining to a diagnosis using a capsule endoscope, but a diagnosis in an endoscopic examination including a common endoscope depends largely on a subject of a physician, and thus desired is an implementation of a computer aided diagnosis (CAD) detecting an existence of a diseased focus for the purpose of improving a quality of an image diagnosis and shortening a radiogram interpretation time. Such an endoscopic diagnosis support apparatus utilizing the CAD is for presenting, to a physician, as to what finding or lesion an image as a diagnosis target is categorized by using various characteristic quantities calculated from a region of interest (ROI) within an image and using a threshold value process or a statistical/non-statistical identifier, thereby supporting an objective and quantitative diagnosis; and by selecting an image suspicious of a disease, thereby alleviating a load on the physician interpreting a radiogram.

In a diagnosis using such an endoscopic image, various pathological rationales can be considered on an existence of a bleeding, and a number of approaches have accordingly been employed for detecting a bleeding.

As one of them, disclosed is a method of presetting sample values of hue, saturation and brightness of a bleeding region, and those of hue, saturation and brightness of a normal mucous membrane for the same image as the bleeding region, and judging a closeness of the value of the target region to either region, thereby discerning whether it is the normal mucous membrane or a bleeding region (refer to a patent document 1 for example).

Patent document 1: International disclosure No. 02/073507 brochure

SUMMARY OF THE INVENTION

However, the method of presetting sample values of hue, saturation and brightness of a bleeding region and those of hue, saturation and brightness of a normal mucous membrane for the same image as the bleeding region, and judging a closeness of the value of the target region to either region, thereby discerning whether it is the normal mucous membrane or a bleeding region, has been faced with the problem of the discernment result depending on the sample value.

In consideration of the situation as described above, the purpose of the present invention is to provide an endoscopic diagnosis support method, an endoscopic diagnosis support apparatus, and an endoscopic diagnosis support program, all of which are capable of extracting an image picking up a bleeding region easily and accurately from among a large number of endoscopic images picked up by an endoscope observation apparatus.

In order to solve the problem described above, the present invention has adopted the following comprisals.

That is, according to first aspect of the present invention, an endoscopic diagnosis support method of the present invention is one which is carried out in an endoscopic diagnosis support apparatus for supporting an endoscopic diagnosis performed based on an endoscopic image picked up by an endoscope observation apparatus, comprising: calculating a tone from a color signal of each of plural image zones obtained by dividing the endoscopic image; and discerning an image zone including a bleeding region by judging a difference among each of the plural image zones based on a tone of the calculated each image zone.

Also according to second aspect of the present invention, an endoscopic diagnosis support apparatus of the present invention is one for supporting an endoscopic diagnosis carried out based on an endoscopic image picked up by an endoscope observation apparatus, comprising: a tone calculation unit for calculating a tone from a color signal of each of plural image zones obtained by dividing the endoscopic image; and a bleeding region discernment unit for discerning an image zone including a bleeding region by judging a difference among each of the plural image zones based on a tone of each image zone calculated by the tone calculation unit.

Also according to third aspect of the present invention, an endoscopic diagnosis support program, or an endoscopic diagnosis support program product, of the present invention is one for making an endoscopic diagnosis support apparatus carry out an endoscopic diagnosis performed based on an endoscopic image picked up by an endoscope observation apparatus, wherein the program makes the endoscopic diagnosis support apparatus carry out the procedures of: calculating a tone from a color signal of each of plural image zones obtained by dividing the endoscopic image; and discerning an image zone including a bleeding region by judging a difference among each of the plural image zones based on a tone of the calculated each image zone.

BRIEF DESCRIPTION OF THE DRAWINGS

The present invention will be more apparent from the following detailed description when the accompanying drawings are referenced.

FIG. 2 is a diagram for describing a system comprisal of an endoscopic diagnosis support apparatus 7;

FIG. 3 is a flow chart showing a flow (part 1) of an endoscopic diagnosis support process carried out by an endoscopic diagnosis support apparatus 7 to which the present invention is applied;

FIG. 7 is a flow chart showing a process for calculating an average value based on an area only of a normal mucous membrane;

FIG. 11 is a flow chart showing a flow of an endoscopic diagnosis support process for identifying a bleeding region existing in a mucous membrane area having a chromaticity of yellow.

DESCRIPTION OF THE PREFERRED EMBODIMENTS

The following is a description of the preferred embodiment of the present invention by referring to the accompanying drawings.

Figure 1:
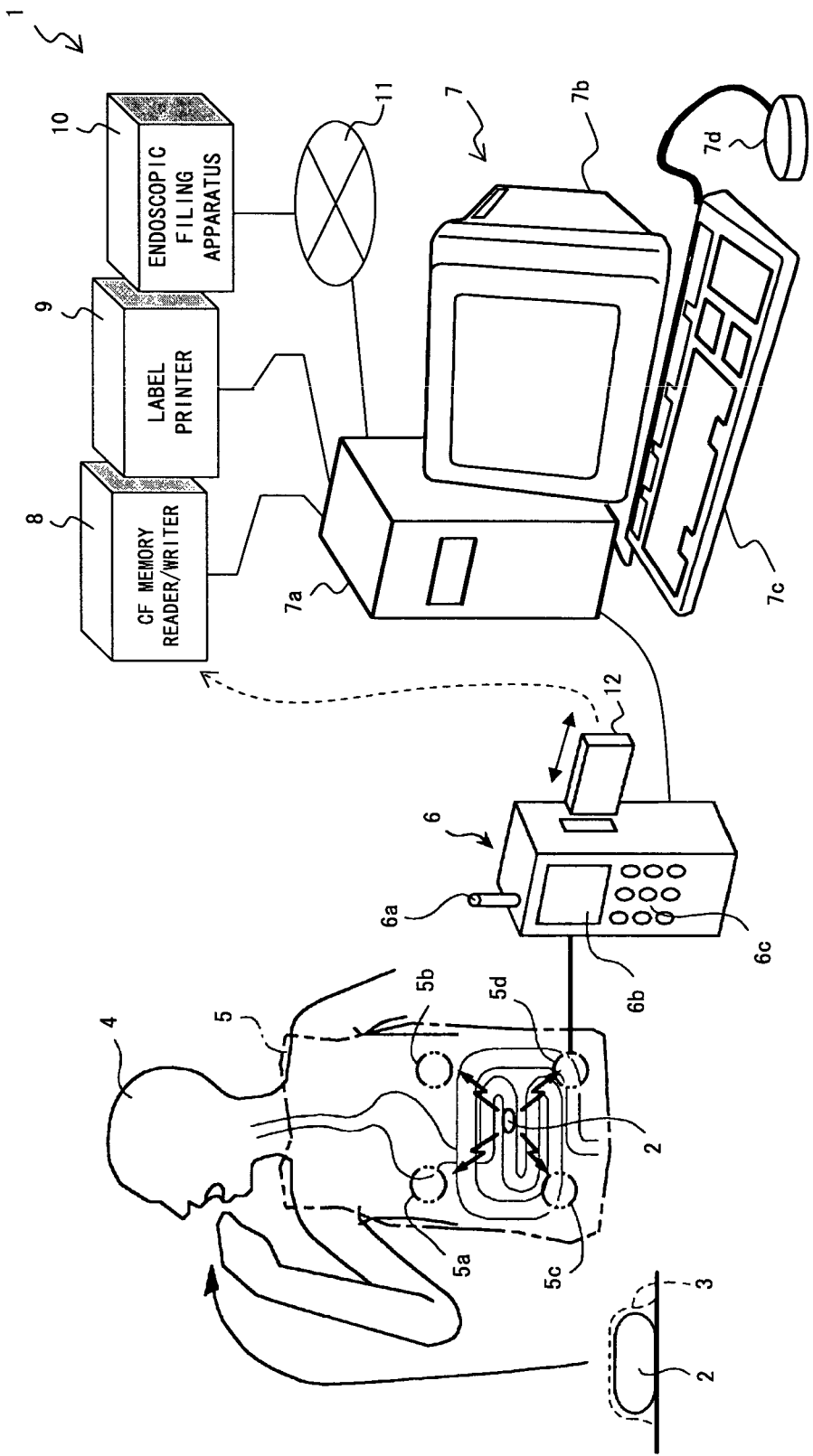
FIG. 1 is an overall configuration diagram of a capsule endoscope system including an endoscopic diagnosis support apparatus to which the present invention is applied.

FIG. 1 is an overall configuration diagram of a capsule endoscope system including an endoscopic diagnosis support apparatus to which the present invention is applied.

Referring to FIG. 1, the capsule endoscope system 1 comprises a capsule type endoscope observation apparatus 2 packaged in a package 3, a jacket 5 to be worn by a patient 4, a receiver 6 detachably attached to the jacket 5, an endoscopic diagnosis support apparatus 7 applied by the present invention, a Compact Flash (CF; a registered trademark) memory reader/writer 8, a label printer 9, an endoscopic filing apparatus 10, and a network 11 such as LAN.

The endoscope observation apparatus 2 is equipped with an image pickup unit, a radio communication unit, et cetera (neither is shown herein), so as to enable the radio communication unit to externally transmit image information (i.e., image information representing a pickup image) picked up by the image pickup unit.

The jacket 5 is equipped with antennas 5a, 5b, 5c and 5d for capturing a radio wave of image information of a pickup image transmitted from the radio communication part equipped in the endoscope observation apparatus 2, enabling a wireless or wired communication with the receiver 6.

The receiver 6 is equipped with an antenna 6a for use in the case of wirelessly receiving image information directly from the jacket 5, a display unit 6b for displaying information necessary for an observation (or examination) and an input unit 6c for inputting information necessary for an observation (or examination). Also, a CF memory 12 storing received image information can be detachably attached to the receiver 6.

The endoscopic diagnosis support apparatus 7 comprises such as a main body 7a, a display apparatus 7b, a key board 7c, a mouse 7d being furnished with a process function for a physician, et al, to perform a diagnosis based on an image of an organ, et cetera, within a patient's body photographed by the endoscope observation apparatus 2. The endoscopic diagnosis support apparatus 7, being equipped with an interface for connecting communicably to the receiver 6, CF memory reader/writer 8 and label printer 9, respectively, performs a read from the CF memory 12 and write thereto, a patient card printing, et cetera. Also, the endoscopic diagnosis support apparatus 7 displays an image of an organ, et cetera, in a display unit 7b based on image information of a pickup image of the inside of a patient body, which is transferred from the receiver 6 for example. Furthermore, the endoscopic diagnosis support apparatus 7, comprising a communication function for connecting to a network 11, accumulates an examination result, et cetera, of a patient in the endoscopic filing apparatus 10 by way of the network 11. Note that the endoscopic filing apparatus 10 may be integrally incorporated in the endoscopic diagnosis support apparatus 7.

As shown in FIG. 1, the endoscope observation apparatus 2 is taken out of the package 3 and the present endoscope observation apparatus 2 is swallowed by the patient 4 prior to starting an examination, then the present endoscope observation apparatus 2 passes through the esophagus, progresses in the body cavity aided by the peristalsis of the digestive tract while picking up images of the body cavity in an orderly fashion.

And, a radio wave carrying image information representing a pickup image resulting from the image pick-up is output from the endoscope observation apparatus 2 and captured by the individual antennas 5a, 5b, 5c and 5d, which are equipped on the jacket 5, on an as required basis or at an appropriate time. A signal from an antenna 5a, 5b, 5c or 5d with a high radio wave reception intensity is transmitted to the receiver 6 placed externally to the body of the patient 4.

In the receiver 6, pieces of image information of sequentially received pickup images are stored in the CF memory 12. Note that the receiver 6 is not synchronous with an image pickup start of the endoscope observation apparatus 2, and instead a reception start and a reception end are controlled by operations of an input unit 6c. As for image information of the pickup image, the assumption here is the image information of a still image, although it may be the image information of still images picked up at a plurality of frames per second for displaying a 1a dynamic image, or image information of a normal dynamic image.

When ending an observation (or examination) of the patient 4 by the endoscope observation apparatus 2, the image information of the pickup image stored in the CF memory 12 is transferred to the endoscopic diagnosis support apparatus 7 by way of a cable. Or, a configuration may be such that the CF memory 12 storing image information of the pickup image is mounted on the CF memory reader/writer 8 and the image information of the pickup image is transferred to the endoscopic diagnosis support apparatus 7 by way of the CF memory reader/writer 8.

At the endoscopic diagnosis support apparatus 7, the transferred image information of the pickup image is stored for each patient, the image information of the pickup image of a specific patient is read on an as required basis and it is displayed in the display unit 7b as an image. This configuration enables an acquisition of useful data for a physiological research and a diagnosis of a lesion all across the digestive tract of the human body including deep parts (such as the small intestine) which can never be reached by an ultrasonic wave scope, a common endoscope, or other means.

Incidentally, the endoscope observation apparatus 2 is for moving with the peristaltic movement of the digestive tract cavity as described above, and therefore it picks up image in the repetition of movement and stoppage. Therefore, the total number of images related to image information picked up in the interim is enormous; yet the images continuing in a time series, however, have a characteristic of a large number thereof being the same or approximately the same image.

The endoscopic diagnosis support apparatus 7 is configured to display suitably for easily grasping a large number of images and for easily finding out a desired image, for example, an image of a diseased region, from among the large number of images.

The next is a further detailed description of a comprisal and operation of the present endoscopic diagnosis support apparatus 7.

FIG. 2 is a diagram for describing a system comprisal of the endoscopic diagnosis support apparatus 7.

Referring to FIG. 2, a main body 7a of the endoscopic diagnosis support apparatus carrying out an image process and information process generally uses a personal computer (PC), generates image data from an image signal output from the endoscope observation apparatus 2 which outputs the image signal by picking up image within a live body, obtains image data, by way of the network 11, stored in the endoscopic filing apparatus 10 that accumulates the generated image data, applies various processes to the image data and displays the process result in the display apparatus 7b. A designation of image data to be processed, an obtainment and display of the designated image data, and an instruction of process execution are conducted by the operations on an operation apparatus comprising a key board 7c and a mouse 7d.

Meanwhile, the main body 7a comprises a central processing unit (CPU) 23 executing a control and a process; memory 24 for storing a process program and data; an external storage interface (I/F) 25 for reading and writing information from and to a storage apparatus 7e constituted by a hard disk; a network card 21 for carrying out communications with external equipment; an operation I/F 22 for carrying out an input and output with an operation apparatus; a graphic board 26 for outputting a video signal to the display apparatus 7b; and a bus 27 interconnecting the aforementioned components so as to enable mutual communications among them.

The network card 21 is for exchanging data with the endoscopic filing apparatus 10 connected to a LAN. The operation I/F 22 receives an input signal input by the keyboard 7c and mouse 7d, which are operation apparatus, and carries out a necessary data process.

The storage apparatus 7e, being connected to the main body 7a, stores the endoscopic diagnosis support program for carrying out an analysis process. The endoscopic diagnosis support program, comprising a plurality of execution files, a dynamic link library file or a setup file, calculates a tone from a color signal of each of plural image zones obtained by dividing an endoscopic image and judges a difference among the plural image zones based on the calculated tone of each image zone, thereby discerning an image zone including a bleeding region.

The external storage I/F 25 reads the endoscopic diagnosis support program stored in the storage apparatus 7e and stores it in the memory 24.

The CPU 23 executes the endoscopic diagnosis support program stored in the memory 24, thereby obtaining an endoscopic image and performing an image analysis process including an endoscopic diagnosis support process.

The next is a description on an operation of the endoscopic diagnosis support carried out by the endoscopic diagnosis support apparatus 7 by referring to FIGS. 3 through 12. Note that the operation of the present endoscopic diagnosis support is carried out by the CPU 23 reading, and executing, the control program pre-stored in the ROM 24.

FIG. 3 is a flow chart showing a flow (part 1) of an endoscopic diagnosis support process carried out by an endoscopic diagnosis support apparatus 7 to which the present invention is applied.

The endoscopic diagnosis support process shown in FIG. 3 is for calculating an average chromaticity in image information and identifying a bleeding region based on a chromaticity deviation from the calculated average chromaticity or an absolute chromaticity.

First, in the step S31, the endoscopic diagnosis support apparatus 7 obtains image information picked up by the endoscope observation apparatus 2 from the endoscopic filing apparatus 10 or the storage apparatus 7e which has received the data therefrom.

In the step S32, the CPU 23 divides the image data obtained in the step S31 into plural zones (e.g., M by N pieces). Here, "divide into plural zones" means dividing an example image data of "288 pixels vertical by 288 pixels horizontal" into 36 vertical by 36 horizontal pieces of zones by the size of "8 pixels vertical by 8 pixels horizontal". In this case, M=36, and N=36.

In the steps S33 through S36, the CPU 23 calculates a chromaticity of each zone divided in the step S32. That is, it starts the process by substituting "1" for the variable i in the step S33, followed by calculating a ratio of the green component to red component (i.e., $g/r(i)=G(i)/R(i)$), and a ratio of the blue component to green component (i.e., $b/g(i)=B(i)/G(i)$), of the three primary colors as a chromaticity of the i-th zone (where i=1 through M*N) in the steps S34 and S35.

Then in the step S37, it calculates an average value $Mg/r$ of the $g/r(i)$, and an average value $Mb/g$ of the $b/g(i)$, where i=1 through M*N, which are calculated in the step S35.

Then in the steps S38 through S42, the CPU 23 judges whether or not each zone divided in the step S32 includes a bleeding region. That is, in the step S38, it starts the process by substituting "1" for the variable i, and in the step S39 judges whether or not a g/r(i) is smaller than a resultant value of a predetermined margin added to the Mg/r and also a b/g(i) is larger than a resultant value of a predetermined margin added to the Mb/g. If the judgment is that the g/r(i) is smaller than the resultant value of a predetermined margin (e.g., −0.01) added to the Mg/r and also if the b/g(i) is larger than the resultant value of a predetermined margin (e.g., −0.01) added to the Mb/g ("yes" for the step S39), it judges that the i-th zone includes a bleeding zone in the step S40.

Figure 4:
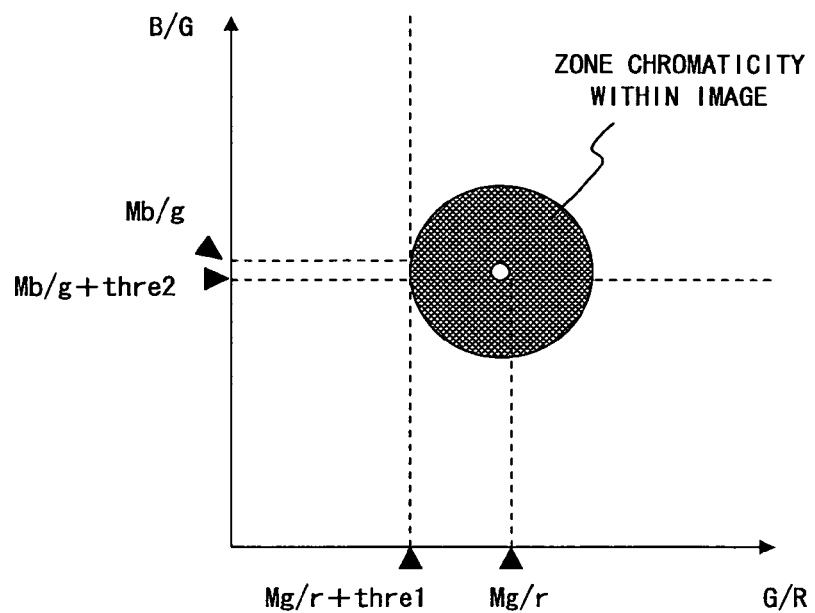
FIG. 4 is a chromaticity distribution diagram of an image not including a bleeding region.
Figure 5:
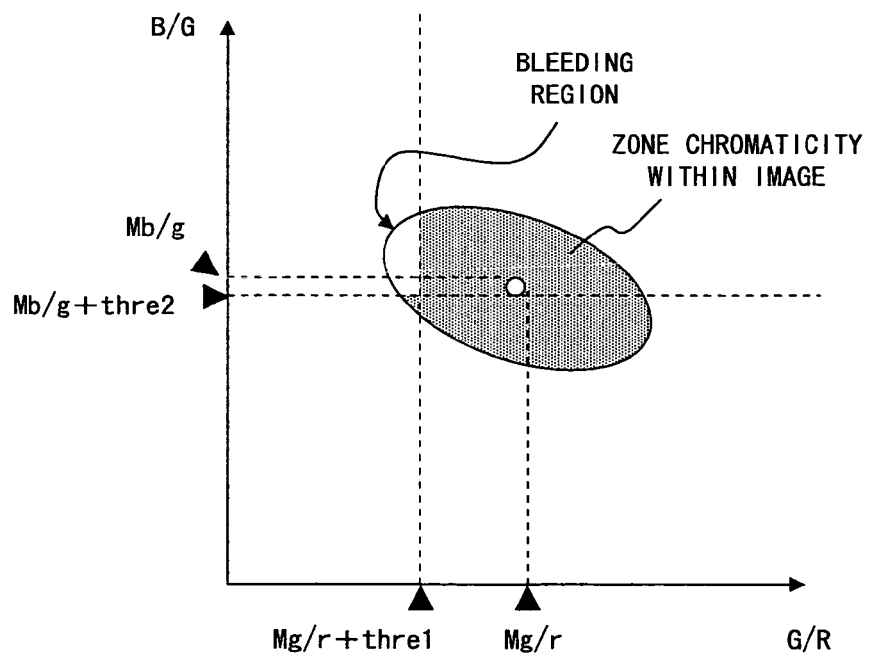
FIG. 5 is a chromaticity distribution diagram of an image including a bleeding region.

The reason for adding a predetermined margin to the Mg/r and likewise to the Mb/g is that a zone in which a ratio of blue component to red component is smaller than a resultant value of a predetermined margin added to the average value Mg/r and also a ratio of blue component to green component is larger than a resultant value of a predetermined margin added to the average value Mb/g indicates a bleeding zone, as is apparent from the chromaticity distribution diagram of an image not including a bleeding region shown in FIG. 4 and that of an image including a bleeding region shown in FIG. 5. Meanwhile, if the g/r(i) is smaller than a predefined absolute bleeding threshold value Zg/r and also the b/g(i) is larger than a predefined absolute bleeding threshold Zb/g, the i-th zone may be judged as including a bleeding region, independent of the average value Mg/r or Mb/g. This configuration makes it possible to judge an existence of a bleeding region even if the averages Mg/r and Mb/g are biased toward a zone of bleeding region due to an existence of a large bleeding area.

The above is a description on the endoscopic diagnosis support process for identifying a bleeding region by calculating an average chromaticity in image information and based on a chromaticity deviation from the calculated average chromaticity, or an absolute chromaticity.

However, a mucous membrane average value of an image is biased toward a bleeding region in image data in which a bleeding region exists, and therefore there is a possibility of erroneous identification of a bleeding region as a result of using a chromaticity deviation from the biased average value.

Accordingly described here is an endoscopic diagnosis support process capable of calculating an image mucous membrane average value from image data of normal mucous membrane which is only a little influenced by a bleeding region or a foreign material.

Figure 6:
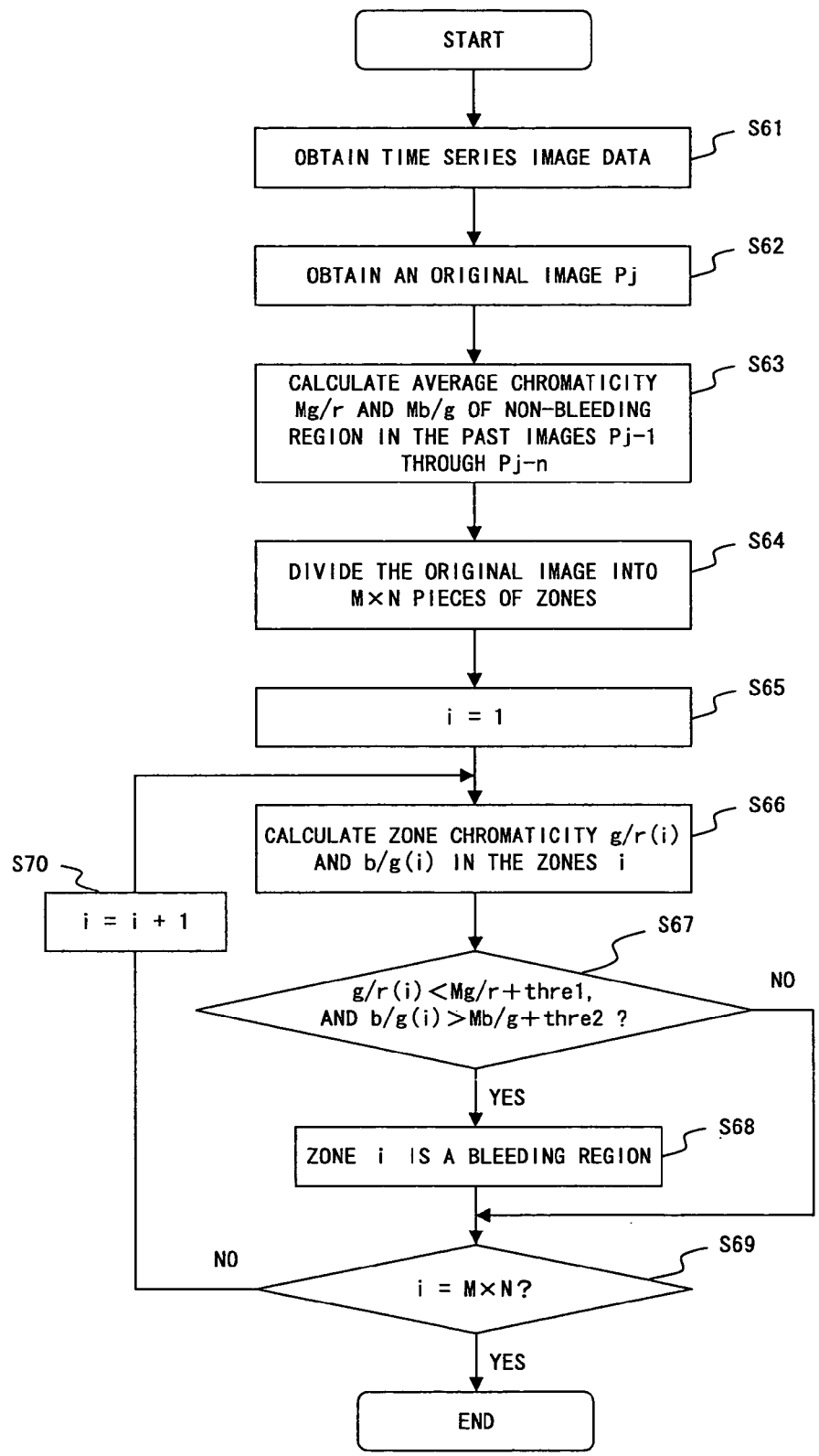
FIG. 6 is a flow chart showing a flow (part 2) of an endoscopic diagnosis support process carried out by an endoscopic diagnosis support apparatus 7 to which the present invention is applied.

FIG. 6 is a flow chart showing a flow (part 2) of an endoscopic diagnosis support process carried out by an endoscopic diagnosis support apparatus 7 to which the present invention is applied.

First, in the steps S61 through S63, the CPU 23 calculates a mucous membrane average value by using past image data obtained in time series. Specifically, in the step S61, it obtains all of the image data obtained in the past in time series, followed by obtaining a discretionary piece of image data Pj in the step S62, and calculating the averages of chromaticity Mg/r and Mb/g by using data of a zone (i.e., a zone that is a non-bleeding region) other than the one which is already judged by the endoscopic diagnosis support process as including a bleeding region, of pieces of image data from one piece prior to the discretionary image data Pj to n-pieces prior in time series, that is, between image data Pj−1 and Pj−n in the step S63.

In the next step S64, the CPU 23 divides the image data Pj obtained in the step S63 into plural (e.g., M*N pieces) zones, e.g., dividing image data of 288 pixels vertical by 288 pixels horizontal into 36 vertical by 36 horizontal pieces of zones by the size of 8 pixels vertical by 8 pixels horizontal.

In the steps S65 through S70, it calculates a chromaticity of each zone divided in the step S62 and judges whether or not each zone includes a bleeding region. That is, it starts the process by substituting "1" for the variable i in the step S65, followed by calculating a ratio of the green component to red component (i.e., g/r(i)=G(i)/R(i)), and a ratio of the blue component to green component (i.e., b/g(i)=B(i)/G(i)), of the three primary colors as a chromaticity in the i-th zone (where i=1 through M*N) in the step S66. Then in the step S67, it judges whether or not the g/r(i) is smaller than a resultant value of a predetermined margin added to the Mg/r and also the b/g(i) is larger than a resultant value of a predetermined margin added to the Mb/g. If the judgment is that the g/r(i) is smaller than the resultant value of a predetermined margin (e.g., −0.01) added to the Mg/r and also if the b/g(i) is larger than the resultant value of a predetermined margin (e.g., −0.01) added to the Mb/g ("yes" for the step S67), the CPU 23 judges that the i-th zone includes a bleeding zone in the step S68.

As such, an endoscopic diagnosis support process based on the average chromaticity of the normal mucous membrane in an observation target region can be carried out by calculating the average chromaticity Mg/r and Mb/g based on the past image data which has been obtained in time series and already judged whether or not a bleeding region is included.

It is also possible to limit to zones belonging to the normal mucous membrane among divided zones and calculate an average value of these zones.

FIG. 7 is a flow chart showing a process for calculating an average value based on an area only of a normal mucous membrane.

First, in the step S71, the endoscopic diagnosis support apparatus 7 obtains image information picked up by the endoscope observation apparatus 2 from the endoscopic filing apparatus 10 or the storage apparatus 7e which has received the data therefrom.

In the next step S72, the CPU 23 divides the image data obtained in the step S71 into plural (e.g., M*N pieces) zones, e.g., dividing image data of 288 pixels vertical by 288 pixels horizontal into 36 vertical by 36 horizontal pieces of zones by the size of 8 pixels vertical by 8 pixels horizontal.

In the steps S73 through S78, it calculates a chromaticity of each zone divided in the step S72 and judges whether or not each zone is a normal mucous membrane. That is, it starts the process by substituting "1" for the variable i in the step S73, followed by calculating a ratio of the green component to red component (i.e., g/r(i)=G(i)/R(i)), and a ratio of the blue component to green component (i.e., b/g(i)=B(i)/G(i)), of the three primary colors as a chromaticity in the i-th zone (where i=1 through M*N) in the step S74. Then in the step S75, it judges whether or not the g/r(i) is larger than a predefined value (thre11) and whether or not the b/g(i) is larger than a predefined value (thre12). If the judgment is that the g/r(i) is larger than a predefined value (thre11) and that the b/g(i) is larger than a predefined value (thre12) ("yes" for the step S75), the CPU 23 judges that the i-th zone is the normal mucous membrane and raises a flag (i.e., a value NEN is substituted for the variable flag) in the step S76.

Then in the step S79, it calculates the average chromaticity Mg/r and Mb/g related to the zone which is judged as the normal mucous membrane, that is, the one in which a value NEN is substituted for the variable flag.

It is also possible to calculate an average value related to the center area of a distribution which is deemed to be less influenced by a bleeding region or foreign material by referring to a chromaticity distribution of divided zones.

Figure 8:
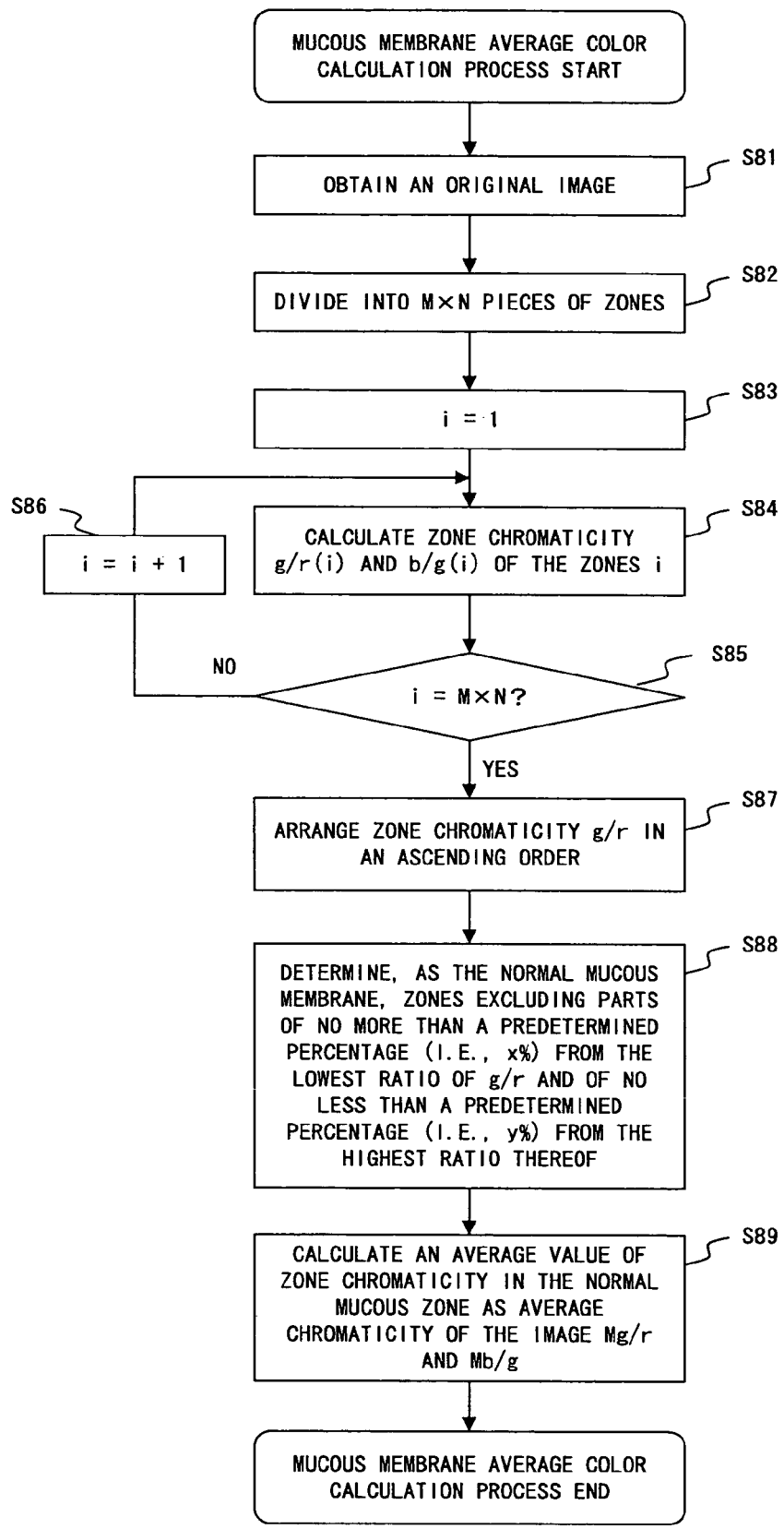
FIG. 8 is a flow chart showing a process for calculating an average value based on an area related to the center area of a chromaticity distribution.
Figure 9:
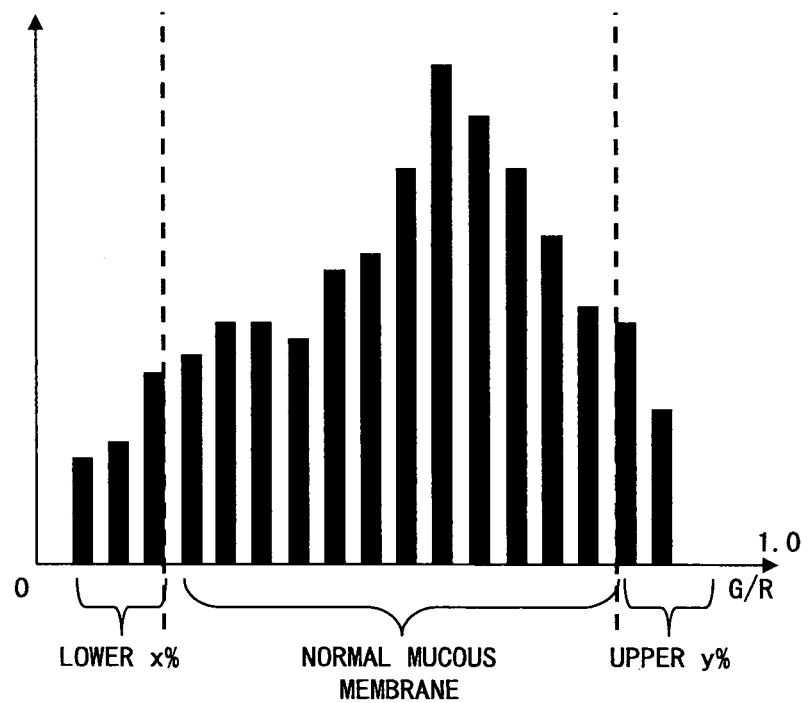
FIG. 9 is a diagram showing a distribution of a ratio of a green component to a red component, i.e., $g/r(i)$.

FIG. 8 is a flow chart showing a process for calculating an average value based on an area related to the center area of a chromaticity distribution.

First, in the step S81, the endoscopic diagnosis support apparatus 7 obtains image information picked up by the endoscope observation apparatus 2 from the endoscopic filing apparatus 10 or the storage apparatus 7e which has received the data therefrom.

In the next step S82, the CPU 23 divides the image data obtained in the step S81 into plural (e.g., M*N pieces) zones, e.g., dividing image data of 288 pixels vertical by 288 pixels horizontal into 36 vertical by 36 horizontal pieces of zones by the size of 8 pixels vertical by 8 pixels horizontal.

In the steps S83 through S86, it calculates a chromaticity of each zone divided in the step S82 and judges whether or not each zone is a normal mucous membrane. That is, it starts the process by substituting "1" for the variable i in the steps S83, followed by calculating a ratio of the green component to red component (i.e., g/r(i)=G(i)/R(i)), and a ratio of the blue component to green component (i.e., b/g(i)=B(i)/G(i)), of the three primary colors as a chromaticity in the i-th zone (where i=1 through M*N) in the steps S84 and S85.

Then in the step S87, it lines up the ratios of the green component to red component, i.e., g/r(i), among the chromaticity of each zone calculated in the step S84, in an ascending order (refer to FIG. 9), and in the step S88 it determines, as the normal mucous membrane, zones excluding parts of no more than a predetermined percentage (i.e., x %) from the lowest ratio of g/r(i) and parts of no less than a predetermined percentage (i.e., y %) from the highest ratio thereof (refer to FIG. 9), followed by calculating an average value Mg/r related to the zone determined as the normal mucous membrane in the step S88 and an average value Mb/g of the b/g(i) in the step S89.

The next is a description on an endoscopic diagnosis support process capable of reducing an erroneous extraction of a bleeding region due to a chromaticity variation of a mucous membrane influenced by a villus area or a chronic disease area such as gastritis.

The process flow is a similar to the case of FIG. 3 or FIG. 6, except for a different condition for extracting a zone including a bleeding region. That is, the predetermined margins are respectively different in the condition "whether or not the g/r(i) is smaller than a resultant value of a predetermined margin added to the Mg/r and also the b/g(i) is larger than a resultant value of a predetermined margin added to the Mb/g" as shown in the step S39 of FIG. 3 or the step S67 of FIG. 6.

In the example shown in FIG. 3 or 6, the predetermined margin added to the Mg/r is "−0.01" and the one added to the Mb/g is also "−0.01", whereas a predetermined margin added to the Mg/r is "−0.01−A" and one added to the Mb/g is "−0.01+B" in this event.

The variable A is a k multiplied by standard deviation of values of g/r(i) in the surrounding area of the divided areas i, and the variable B is a k multiplied by a standard deviation of values of b/g(i) in the surrounding area of the divided areas i. That is, the condition for extracting a bleeding region is stricter in an area with a larger deviation, thus making it possible to reduce an erroneous detection of a bleeding region due to a chromaticity variation of a mucous membrane influenced by a villus area or a chronic disease area such as gastritis.

Alternatively, the variable A may choose a k multiplied by variation coefficient of values of g/r(i) in the surrounding area of the divided areas i, and the variable B may also choose a k multiplied by variation coefficient of values of b/g(i) in the surrounding area of the divided areas i.

Figure 10:
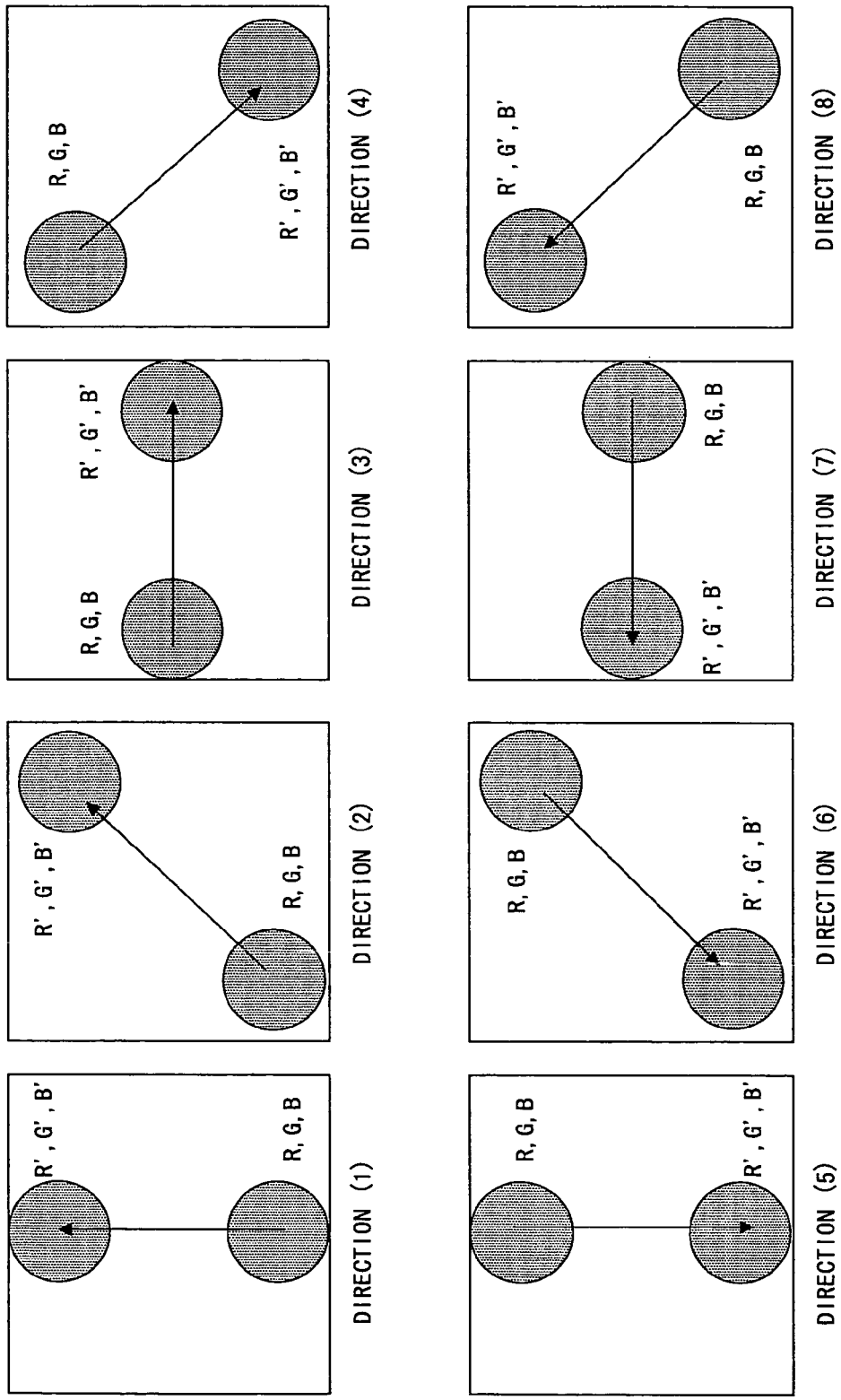
FIG. 10 is a diagram showing a positional relationship of areas.

Or, the variable A may choose a k multiplied by a maximum value of a G-variation/R-variation in eight directions (i.e., directions (1) through (8) shown in FIG. 10) within a divided area i, and the variable B may choose a k multiplied by a maximum value of a B-variation/G-variation in eight directions (i.e., directions (1) through (8) shown in FIG. 10), as shown in FIG. 10. Note that the G-variation=loge(G')−loge(G), and R-variation=loge(R')−loge(R) in this event.

Or, the variables A and B may use a k multiplied by a gradient in the divided areas i.

The next is a description of an example of identifying a bleeding region existing in a mucous membrane area having a chromaticity of yellow covered with intestinal fluids, et cetera. A chromaticity deviation of a bleeding region existing in a mucous membrane area having a chromaticity of yellow covered with intestinal fluids, et cetera has a different characteristic from that of a bleeding region existing in the normal mucous membrane area, and therefore a condition for identifying a bleeding region needs to be changed.

FIG. 11 is a flow chart showing a flow of an endoscopic diagnosis support process for identifying a bleeding region existing in a mucous membrane area having a chromaticity of yellow.

First, in the step 111, the endoscopic diagnosis support apparatus 7 obtains image information picked up by the endoscope observation apparatus 2 from the endoscopic filing apparatus 10 or the storage apparatus 7e which has received the data therefrom.

In the next step S112, the CPU 23 divides the image data obtained in the step S111 into plural (e.g., M*N pieces) zones, e.g., dividing image data of 288 pixels vertical by 288 pixels horizontal into 36 vertical by 36 horizontal pieces of zones by the size of 8 pixels vertical by 8 pixels horizontal.

In the steps S113 through S116, the CPU 23 calculates a chromaticity of each zone divided in the step S112. That is, it starts the process by substituting "1" for the variable i in the step S113, followed by calculating a ratio of the green component to red component (i.e., g/r(i)=G(i)/R(i)), and a ratio of the blue component to green component (i.e., b/g(i)=B(i)/G(i)), of the three primary colors as a chromaticity in the i-th zone (where i=1 through M*N) in the steps S114 and S115.

Then in the step S117, it calculates an average value Mg/r of the g/r(i), and an average value Mb/g of the b/g(i), where i=1 through M*N, which are calculated in the step S115.

Then the CPU 23 judges whether or not the average value Mg/r calculated in the step S117 is smaller than a predetermined value ($\alpha$) in the step S118 and, if the judgment is that it is smaller ("yes" for the step S118), determines that the image data represents an image of a mucous membrane having a chromaticity of yellow covered with intestinal fluids or the like.

Lastly, the CPU 23 judges whether or not each of the zones divided in the step S112 includes a bleeding region in the steps. S120 through S124. That is, in the step S120, it starts the process by substituting "1" for the variable i, and in the step S121 judges whether or not a g/r(i) is smaller than a resultant value of a predetermined margin added to the Mg/r and also a b/g(i) is larger than a resultant value of a predetermined margin added to the Mb/g. If the judgment is that the g/r(i) is smaller than the resultant value of a predetermined margin (e.g., −0.01) added to the Mg/r and also if the b/g(i) is larger than the resultant value of a predetermined margin (e.g., 0.03) added to the Mb/g ("yes" for the step S121), it judges that the i-th zone includes a bleeding zone in the step S122.

The next is a description on an example of classifying the divided zones of the image into a plurality of categories, calculating an average chromaticity of mucous membrane for each category and differentiating a condition for extracting a bleeding region depending on the category. This example makes it possible to select the most optimum extraction condition in the case of zones belonging to a plurality of categories intermingling in a single image, hence improving accuracy in extracting a bleeding region.

Figure 12:
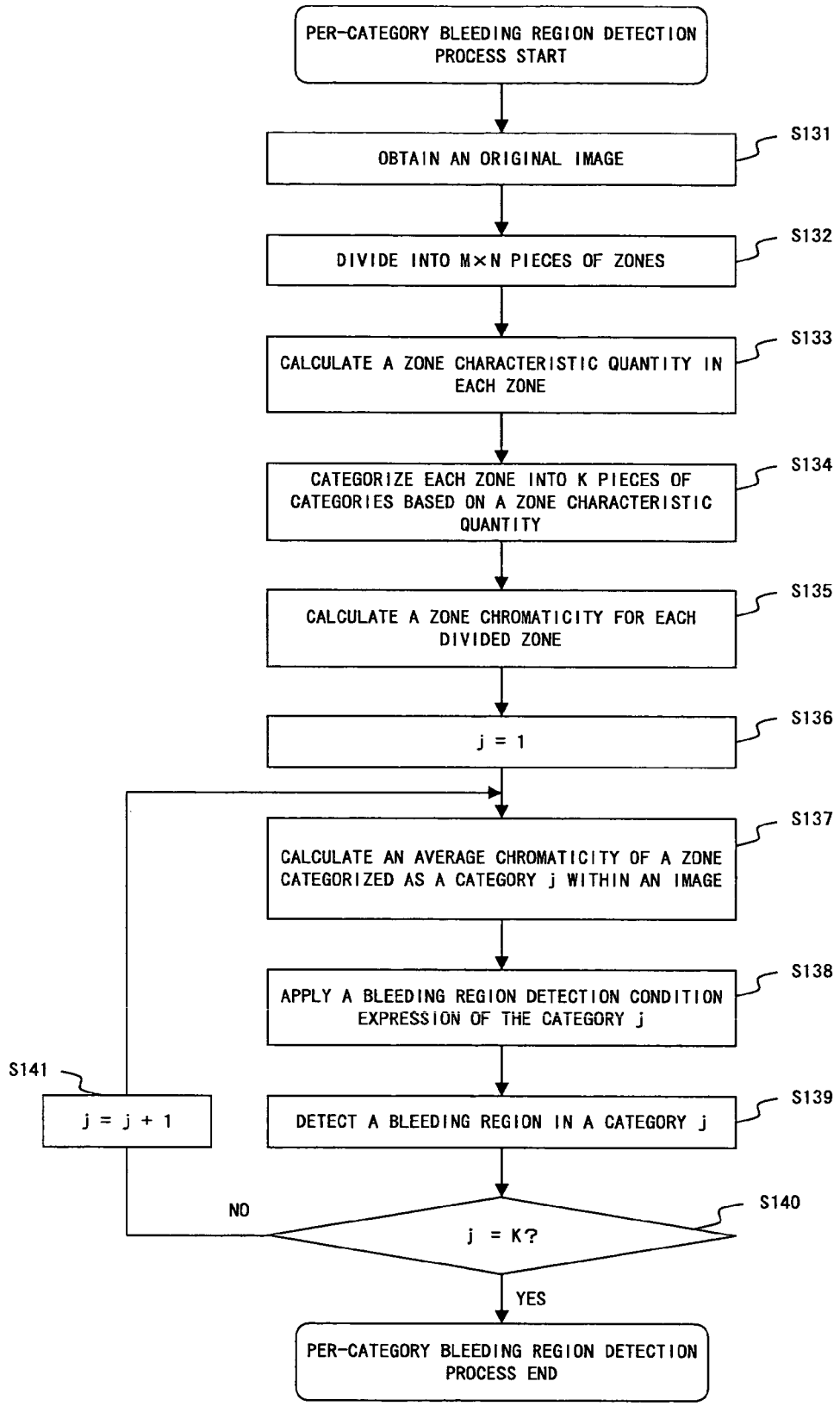
FIG. 12 is a flow chart showing a flow of an endoscopic diagnosis support process of an example in which conditions for extracting a bleeding region are different individually for a plurality of categories.

FIG. 12 is a flow chart showing a flow of an endoscopic diagnosis support process of an example in which conditions for extracting a bleeding region are different individually for a plurality of categories.

First, in the step 131, the endoscopic diagnosis support apparatus 7 obtains image information picked up by the endoscope observation apparatus 2 from the endoscopic filing apparatus 10 or the storage apparatus 7e which has received the data therefrom.

In the next step S132, the CPU 23 divides the image data obtained in the step S131 into plural zones (e.g., M by N pieces). Here, "divide into plural zones" means dividing an example image data of "288 pixels vertical by 288 pixels horizontal" into 36 vertical by 36 horizontal pieces of zones by the size of "8 pixels vertical by 8 pixels horizontal". In this case, M=36, and N=36.

Then, in the step S133, the CPU 23 calculates a zone characteristic quantity for each zone, for example, a ratio of the blue component to green component (i.e., b/g(i)=B(i)/G(i)), of the three primary colors as a chromaticity in the i-th zone (where i=1 through M*N).

Then in the step S134, it identifies a category to which each zone belongs based on the zone characteristic quantity calculated in the step S133. For example, if a ratio of the blue component to green component, i.e., b/g(i), is larger than a predefined value, it categorizes a category of zone of the normal mucous membrane and accordingly raises a flag (i.e., substituting a variable class (i)=1), while if a ratio of the blue component to green component, i.e., b/g(i), is no more than a predefined value, it categorizes as a zone of yellow mucous membrane and accordingly raises a flag (i.e., substituting a variable class=2; indicating the number of categories K=2). Note that it may be appropriate to calculate a plurality of characteristic quantities as zone characteristic quantities and categorize them into a plurality thereof by using an identifier.

Then, in the step S135 the CPU 23 calculates a zone chromaticity of a divided zone i, for example, g/r(i) and b/g(i), in the i-th zone (where i=1 through M*N) as a zone chromaticity.

Next, in the steps S136 through S141, it judges whether or not each zone of each category, which has been divided in the step S132 and categorized in the step S134, includes a bleeding region. That is, it starts the process by substituting "1" for a variable j in the step S136, followed by calculating, as an average chromaticity for the first category, the average value Mg/r(1) of g/r(i), and the average value Mb/g(1) of b/g(i), of a zone belonging to the first category (i.e., a variable class (i)=1) in the step S137. Then, it applies a bleeding region detection condition expression of the first category to the zone belonging to the first category (i.e., a variable class (i)=1) in the steps S138 and S139. That is, since the first category is the normal mucous membrane, it judges whether or not the g/r(i) is smaller than a resultant value of a predetermined margin added to the Mg/r(1) and also the b/g(i) is larger than a resultant value of a predetermined margin added to the Mb/g (1) in the i-th zone belonging to the first category (i.e., a variable class(i)=1; where i=1 through M*N). If the judgment is that the g/r(i) is smaller than a resultant value of a predetermined margin (e.g., −0.01) added to the Mg/r(1) and also that the b/g(i) is larger than a resultant value of a predetermined margin (e.g., −0.01) added to the Mb/g(1), then the i-th zone is judged to include a bleeding region. Then, it applies a bleeding region detection condition expression of the first category to all zones belonging to the first category among the first to M*N-th zones of the divided zones i, and judges whether or not a bleeding region is included. It then increments the variable j in the step S141, applies the process of the steps S137 through S139 to the second category and thereafter for carrying out the process to all categories, and then ends the process.

As such, the preferred embodiment to which the present invention is applied has been described; an endoscopic diagnosis support apparatus to which the present invention is applied, however, may apparently be a single apparatus, a system or integrated apparatus constituted by a plurality of apparatuses, or a system carrying out a process by way of a network such as LAN and WAN provided that the function of the endoscopic diagnosis support apparatus is carried out, in lieu of being limited to the above described preferred embodiment.

That is, the present invention can adopt various configurations or features possible within the scope thereof, in lieu of being limited to the preferred embodiment described above.

The present invention enables an extraction of an image picking up a bleeding region easily and correctly from among a large number of endoscopic images picked up by an endoscope observation apparatus.

What is claimed is:

1. An endoscopic diagnosis support method carried out in an endoscopic diagnosis support apparatus for supporting an endoscopic diagnosis performed based on an endoscopic image picked up by an endoscope observation apparatus, comprising:
 calculating a first chromaticity and a second chromaticity based on a ratio of color signals that form a three-primary-color signal from a color signal of each of plural image zones obtained by dividing the endoscopic image, wherein the first chromaticity is a ratio of a green component to a red component and wherein the second chromaticity is a ratio of a blue component to the green component; and
 discerning an image zone including a bleeding region by judging that the first chromaticity of each of plural image zones constituting the endoscopic image is smaller than a first resultant value, and that the second chromaticity of each of plural image zones constituting the endoscopic image is larger than a second resultant value, wherein the first resultant value is a sum of: (a) a first predetermined margin that varies dynamically with a variation parameter and (b) an average value of the first chromaticity of all image zones constituting the endoscopic image, and wherein the second resultant value is a sum of: (a) a second predetermined margin that varies dynamically with a variation parameter and (b) an average value of the second chromaticity of all image zones constituting the endoscopic image;
 wherein the variation parameter is a standard deviation, chromaticity variation coefficient, variation value or gradient.

2. The endoscopic diagnosis support method according to claim 1, further comprising:
 selecting an endoscopic image including the discerned image zone.

3. The endoscopic diagnosis support method according to claim 2, further comprising:

calculating an average value by using a center part among a tone distribution of all image zones constituting the endoscopic image when calculating the tone.

4. The endoscopic diagnosis support method according to claim 1, further comprising:
calculating an average value of a tone based on an endoscopic image other than one selected in a past when calculating the tone, and
judging a difference among the plural image zones by comparing the average value calculated based on an endoscopic image other than the past selected endoscopic image with a tone value of each image zone when discerning the bleeding region.

5. The endoscopic diagnosis support method according to claim 1, wherein the variation parameter is the calculated average chromaticity.

6. The endoscopic diagnosis support method according to claim 1, further comprising:
judging a difference among the plural image zones based on a chromaticity deviation from an average value of tones of all image areas constituting the calculated endoscopic image when discerning the bleeding region.

7. The endoscopic diagnosis support method according to claim 6, further comprising:
calculating a chromaticity deviation from an average value of tones based on an endoscopic image other than a past selected endoscopic image when calculating the tone, and
judging a difference among the plural image zones based on a chromaticity deviation calculated based on an endoscopic image other than the past selected endoscopic image when discerning the bleeding region.

8. The endoscopic diagnosis support method according to claim 1, further comprising:
calculating a tone from a color signal of a predetermined image zone among each of plural image zones obtained by dividing the endoscopic image when calculating the tone.

9. An endoscopic diagnosis support apparatus for supporting an endoscopic diagnosis carried out based on an endoscopic image picked up by an endoscope observation apparatus, comprising:
a tone calculation unit for calculating a first chromaticity and a second chromaticity based on a ratio of color signals that form a three-primary-color signal from a color signal of each of plural image zones obtained by dividing the endoscopic image, wherein the first chromaticity is a ratio of a green component to a red component and wherein the second chromaticity is a ratio of a blue component to the green component; and
a bleeding region discernment unit for discerning an image zone including a bleeding region by judging that the first chromaticity of each of plural image zones constituting the endoscopic image is smaller than a first resultant value, and that the second chromaticity of each of plural image zones constituting the endoscopic image is larger than a second resultant value, wherein the first resultant value is a sum of: (a) a first predetermined margin that varies dynamically with a variation parameter and (b) an average value of the first chromaticity of all image zones constituting the endoscopic image, and wherein the second resultant value is a sum of: (a) a second predetermined margin that varies dynamically with a variation parameter and (b) an average value of the second chromaticity of all image zones constituting the endoscopic image; wherein the variation parameter is a standard deviation, chromaticity variation coefficient, variation value or gradient.

10. The endoscopic diagnosis support apparatus according to claim 9, further comprising
a bleeding endoscopic image selection unit for selecting an endoscopic image including an image zone discerned by the bleeding region discernment unit.

11. The endoscopic diagnosis support apparatus according to claim 10, wherein
the tone calculation unit calculates an average by using a center part among a tone distribution of all image zones constituting the endoscopic image.

12. The endoscopic diagnosis support apparatus according to claim 9, wherein
the tone calculation unit calculates an average value of a tone based on an endoscopic image other than one selected in a past by the bleeding endoscopic image selection unit, and
the bleeding region discernment unit judges a difference among the plural image zones by comparing the average value calculated based on an endoscopic image other than the past selected endoscopic image with a tone value of each image zone.

13. The endoscopic diagnosis support apparatus according to claim 9, wherein the variation parameter is the calculated average chromaticity.

14. The endoscopic diagnosis support apparatus according to claim 9, wherein the bleeding region discernment unit judges a difference among the plural image zones based on a chromaticity deviation from an average value of tones of all image areas constituting the calculated endoscopic image.

15. The endoscopic diagnosis support apparatus according to claim 14, wherein the tone calculation unit calculates a chromaticity deviation from an average value of tones based on an endoscopic image other than an endoscopic image selected by the bleeding endoscopic image selection unit, and
the bleeding region discernment unit judges a difference among the plural image zones based on a chromaticity deviation calculated based on an endoscopic image other than the past selected endoscopic image.

16. The endoscopic diagnosis support apparatus according to claim 9, wherein
the tone calculation unit calculates a tone from a color signal of a predetermined image zone among each of plural image zones obtained by dividing the endoscopic image.

17. A computer readable storage device having an endoscopic diagnosis support program for making an endoscopic diagnosis support apparatus carry out support of an endoscopic diagnosis performed based on an endoscopic image picked up by an endoscope observation apparatus, wherein
the program makes the endoscopic diagnosis support apparatus carry out the procedures of:
calculating a first chromaticity and a second chromaticity based on a ratio of color signals that form a three-primary-color signal from a color signal of each of plural image zones obtained by dividing the endoscopic image, wherein the first chromaticity is a ratio of a green component to a red component and wherein the second chromaticity is a ratio of a blue component to the green component;
discerning an image zone including a bleeding region by judging that the first chromaticity of each of plural image zones constituting the endoscopic image is smaller than a first resultant value, and that the second chromaticity of each of plural image zones constituting the endoscopic image is larger than a second resultant value, wherein the first resultant value is a sum of: (a) a first predetermined margin that varies dynamically with a variation parameter and (b) an average value of the first chromaticity of all image zones constituting the endoscopic image, and wherein the second resultant value is a sum of: (a) a second predetermined margin that varies dynamically with a variation parameter and (b) an average value of the second chromaticity of all image zones constituting the endoscopic image;

wherein the variation parameter is a standard deviation, chromaticity variation coefficient, variation value or gradient.

18. An endoscopic diagnosis support apparatus for supporting an endoscopic diagnosis carried out based on an endoscopic image picked up by an endoscope observation apparatus, comprising:

tone calculation means for calculating a first chromaticity and a second chromaticity based on a ratio of color signals that form a three-primary-color signal from a color signal of each of plural image zones obtained by dividing the endoscopic image, wherein the first chromaticity is a ratio of a green component to a red component and wherein the second chromaticity is a ratio of a blue component to the green component; and bleeding region discernment means for discerning an image zone including a bleeding region by judging that the first chromaticity of each of plural image zones constituting the endoscopic image is smaller than a first resultant value, and that the second chromaticity of each of plural image zones constituting the endoscopic image is larger than a second resultant value, wherein the first resultant value is a sum of: (a) a first predetermined margin that varies dynamically with a variation parameter and (b) an average value of the first chromaticity of all image zones constituting the endoscopic image, and wherein the second resultant value is a sum of: (a) a second predetermined margin that varies dynamically with a variation parameter and (b) an average value of the second chromaticity of all image zones constituting the endoscopic image;

wherein the variation parameter is a standard deviation, chromaticity variation coefficient, variation value or gradient.

\* \* \* \* \*